(12) United States Patent
Golledge

(10) Patent No.: US 6,355,322 B1
(45) Date of Patent: Mar. 12, 2002

(54) RELEASE LINER INCORPORATING A METAL LAYER

(75) Inventor: Adrian D. Golledge, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/206,864

(22) Filed: Dec. 8, 1998

(51) Int. Cl.⁷ .............................................. B32B 15/04
(52) U.S. Cl. .............. 428/40.1; 219/121.6; 219/121.67; 219/121.68; 219/121.69; 428/40.9; 428/41.1; 428/41.8; 428/42.2; 428/42.3; 428/138; 428/464
(58) Field of Search ................. 428/40.1, 40.9, 428/41.1, 41.8, 42.2, 42.3, 464, 138; 219/121.6, 121.67, 121.68, 121.69

(56) References Cited

U.S. PATENT DOCUMENTS

| | | | |
|---|---|---|---|
| 3,998,601 A | 12/1976 | Yates et al. .................... 29/195 |
| 4,407,685 A | 10/1983 | Hankland .................... 156/212 |
| 4,995,941 A | * 2/1991 | Nelson ........................ 156/630 |
| 5,153,042 A | 10/1992 | Indrelie ....................... 428/40 |
| 5,167,995 A | 12/1992 | Johnson et al. ............... 428/40 |
| 5,178,924 A | 1/1993 | Johnson et al. ............... 428/40 |
| 5,296,674 A | 3/1994 | Praschek et al. ........ 219/121.69 |
| 5,302,547 A | 4/1994 | Wojnarowski et al. ...... 437/173 |
| 5,313,043 A | 5/1994 | Yamagishi ............. 219/121.68 |
| 5,321,227 A | 6/1994 | Fuchs et al. ........... 219/121.68 |
| 5,328,738 A | 7/1994 | McKillip et al. .............. 428/40 |
| 5,460,863 A | 10/1995 | Kessel et al. ................. 428/40 |
| 5,614,115 A | 3/1997 | Horton et al. ......... 219/121.67 |
| 5,667,708 A | 9/1997 | Glass et al. ............ 219/121.67 |
| 5,681,412 A | 10/1997 | Nedblake et al. ........... 156/184 |
| 5,681,660 A | 10/1997 | Bull et al. ................... 428/500 |
| 5,691,022 A | 11/1997 | Knauf ....................... 428/40.1 |
| 5,695,867 A | 12/1997 | Saitoh et al. ................ 428/219 |
| 5,700,535 A | * 12/1997 | Galsterer ................... 428/40.1 |
| 5,759,422 A | 6/1998 | Schmelzer et al. ............ 216/35 |
| 5,795,649 A | 8/1998 | Cosentino et al. .......... 428/336 |
| 5,800,724 A | 9/1998 | Habeger et al. ............... 216/35 |
| 5,810,957 A | 9/1998 | Boswell ..................... 156/220 |

FOREIGN PATENT DOCUMENTS

| | | |
|---|---|---|
| EP | 0 378 420 | 7/1990 |
| WO | 92/08429 | 5/1992 |

\* cited by examiner

Primary Examiner—Nasser Ahmad
(74) Attorney, Agent, or Firm—Brian E. Szymanski; Harold C. Knecht, III

(57) ABSTRACT

A release liner which includes a metal layer with a release agent attached to a side of the metal layer. The release agent is exposed to releasably receive an article. The metal layer has a thickness sufficient to prevent a laser from penetrating through the metal layer as the article, attached to liner, is laser cut.

11 Claims, 1 Drawing Sheet

RELEASE LINER INCORPORATING A METAL LAYER

FIELD OF THE INVENTION

The present invention relates to a release liner which serves as a carrier for flat or three-dimensional articles, more particularly, to a release liner having a metal layer incorporated into the release liner and, even more particularly, to a release liner having a metal layer of a sufficient thickness to prevent a laser from penetrating through the metal layer as the article is laser cut. This invention also relates to a method of laser cutting an article releasably attached to such a release liner.

BACKGROUND OF THE INVENTION

Paper or polymeric release liners are often utilized as carriers for various products. The products are releasably bonded to the release liner because the products are either inherently tacky or coated with an adhesive. The release liner functions as a carrier for the product as well as a protective layer to prevent contamination of either the adhesive or the back side of the product. The release liner is removed and the product is then applied to another object. The products can be flat or three dimensional and may include decorative designs or indicia. The adhesive or tacky surface on the decorative products enable the application and bonding of the decorative product onto another object for display. Examples of such decorative products include nameplates and graphics for automobiles which are applied to a surface of the vehicle, labels which are applied to various surfaces, and decorative films which cling to surfaces such as windows.

The products are often manufactured on the release liner. In order to improve manufacturing efficiency, the products are produced on either large sheets or webs. It then becomes necessary to cut individual parts or portions of the product from the larger production format. In the past, decorative products have been cut from a sheet or web utilizing steel rule cutting devices, often referred to as either die-cutting or kiss-cutting. This process utilizes a sharp edge that mechanically cuts through the product to a desired depth. This type of cut permits the subsequent removal of the cut portion of the product from the release liner for further processing or direct application onto the desired object. The cutting edge of the mechanical cutting devices are metal and therefore difficult to bend into fine shapes or designs. Thus, they are limited in the degree of detail in which they can cut. Additionally, the cost of fabricating a cutting tool to obtain such fine shapes and designs can be very high.

Thus, there is a need to provide a way to cut decorative products attached to a release liner that enables new and more decorative design patterns with improved economics.

SUMMARY OF THE INVENTION

The present invention provides a release liner for releasably receiving an article. The release liner is utilized as a carrier sheet during the production or formation of the article. The article is then laser cut into a specific shape or pattern. The release liner of the present invention is able to prevent penetration of the laser through the release liner. Without a metal layer in the release liner, a laser may cut through, or at least partially through, the release liner. The cutting of the release liner can result in the undesirable tearing of the release liner upon removal of a cut portion of the product from the liner. This is particularly a problem when it is preferred to first remove the undesirable portion of the article and leave the portion that will later be removed and applied onto another object. The ability to prevent the penetration of the laser enables the cut portion of the article to be removed from the release liner without a significant portion of the liner tearing and pulling away with the article. Preferably, the release liner is prevented from any tearing when the cut portion of the article is removed.

The release liner of the present invention includes a metal layer with a release agent attached to a side of the metal layer. The release agent is exposed to releasably receive an article. The metal has a thickness sufficient to prevent a laser from penetrating through, and preferably into, the metal layer as the article is laser cut. The metal layer is preferably selected from the group consisting of aluminum, copper, iron, tin, or alloys thereof.

The article applied to the release liner of the present invention can be one or more continuous or discontinuous layers of sheet or web material. The article can be produced from various materials that can be laser cut. Preferred articles include adhesive backed articles and non-adhesive backed articles, such as, for example, vinyl or urethane polymers.

The present release liner may optionally include a support layer affixed to one side of the metal layer opposite the release agent. The support layer can assist in forming a rigid release liner. The thickness of the metal layer can then be minimized to a level sufficient to prevent the penetration of the laser. Alternatively, or in addition, the release liner can optionally include an intermediate layer between the metal layer and the release agent.

The method of the present invention includes laser cutting an article while it is adhered to the release liner.

It is an advantage to provide a release liner that is capable of preventing a laser from penetrating into, or at least through, the liner. A release liner that is capable of withstanding a laser enables laser cutting of an article held directly on the release liner. The cut portion of the article may then be removed from the liner without the liner tearing or a portion of the liner separating with the removed portion of the article.

BRIEF DESCRIPTION OF THE DRAWINGS

The above, as well as other advantages of the present invention, will become readily apparent to those skilled in the art from the following detailed description when considered in the light of the accompanying drawings in which.

DETAILED DESCRIPTION

Figure 1:
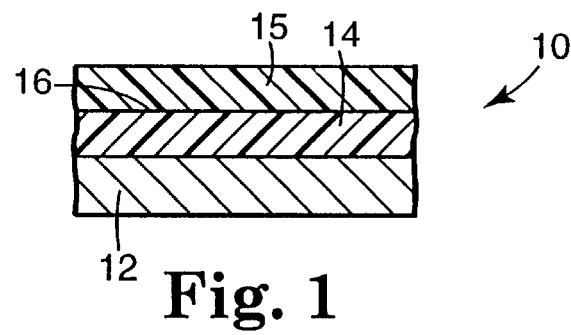
FIG. 1 is a cross-sectional view of a segmented portion of the release liner of the present invention.

The release liner of the present invention includes a metal layer preferably elected from the group consisting of aluminum, copper, iron, tin, and alloys hereof The thickness of the selected metal in the metal layer may vary depending upon the strength of the laser utilized in cutting the article. Additionally, the metal layer must be thick enough to provide some rigidity to the release liner. The rigidity of the release liner is necessary to support an article during either the article manufacturing process or a laminating process wherein the article is attached to the release liner. Preferably, the metal layer is provided as a foil sheet. Additionally, the metal layer may be coated to prevent oxidation of the metal or primed to enhance the adhesion of a release agent to the metal layer. Conventional wash coating compositions and primer compositions are generally recognized in the art and may be suitable for use with the invention.

In accordance with the present invention, the release agent is attached to one side, or a major surface, of the metal layer to releasably receive an article. The release agent is generally tailored to the specific type of article. Certain types of articles require a release agent with a compatible chemical composition in order to achieve an appropriate release force for the desired detachment of the article from the release liner. For example, with an article coated with acrylic adhesive, suitable release agents include silicones, and fluoropolymers, with silicones being a preferred release agent when a low release value is desired. Another example would include the use of an alkyd resin as a release agent for vinyl based compositions, such as vinyl films. Further, an acrylic release agent might be suitable for urethane based articles. Such release agents act to releasably bond these compatible articles to the release liner. Other combinations of conventional release agents and articles may also be suitable for use in the present invention.

Examples of typical release agents include silicones or mixtures of copolymers selected from materials such as silicones, polyurethane, epoxy, acrylics and the like. Additionally, release agents could include polyolefins such as polyethylene and polypropylene, fluoropolymers, polyvinyl carbamates, alkyd resins, and long chain branch polymers such as copolymers of alkyl acrylates which have alkyl side chains of greater than 16 carbon atoms. The preferred release agents include alkyd resins, acrylics, fluoropolymers, polyvinyl carbamates, silicones, and mixtures of copolymers selected from materials such as silicones, polyurethane, epoxy, acrylics and the like.

The articles releasably bonded to the release agent of the present invention often utilize a pressure sensitive adhesive. The release agent of the present invention is then selected to provide the desired release force for the separation of the pressure-sensitive adhesive from the release liner. The pressure-sensitive adhesive is in turn selected to provide an appropriate bond to the article or the base substrate of the article. Useful pressure-sensitive adhesives include acrylic adhesives, tackified block copolymer, tackified natural rubber adhesives, ethylene vinyl acetate adhesives, silicone pressure-sensitive adhesives, and the like.

In general, the release agent of the present invention is applied as a thin layer onto the metal layer. The release agents may be applied onto the metal layer in a solvent or water based system by known methods including roll coating, gravure coating, knife coating, spray coating, and the like. The release agents may also be applied as a 100% solids composition by the same methods as well as by hot melt coating.

The release agent is a layer applied onto the release liner at a preferred thickness of up to about 7 microns. The release agent has a release value sufficient to hold the article to the liner until is desired to remove the article. The release value is the force required to remove a 1 centimeter wide pressure-sensitive adhesive coated article from the release surface according to the Pressure Sensitive Tape Council (PSTC), procedure No. 1. The release values can vary from a very low value of about 2 to 4 grams per centimeter to fairly high values of about 500 grams per centimeter or above. Preferably, pressure-sensitive adhesive backed articles have a release value of about 3 grams per centimeter to about 12 grams per centimeter.

FIG. 1 depicts one embodiment of the present invention. The release liner 10 includes metal layer 12 and release agent 14 attached to one side of the metal layer 12. An article 15 is releasably attached to the surface 16 of the release agent 14.

The release liner of the present invention may optionally include a support layer attached to one side of the metal layer opposite the side upon which the release agent is attached. The support layer is generally utilized to provide rigidity to the liner. The use of the support layer permits the reduction in the thickness of the metal layer to a level sufficient to prevent penetration of the laser. Preferably, the use of the support layer enables the use of a metal layer at a thickness of about 2 microns to about 7 microns.

The support layer may be a paper material, a polymeric material, or a combination thereof. The paper or polymeric material may be supplied in either sheet or web form. Paper is generally included in the release liner at a thickness of about 75 microns to about 175 microns. Preferably, the paper is a calendered, or smooth paper, at about 22.5 kg/ream to about 36.5 kg/ream and a thickness of about 100 microns to about 125 microns. Conventional polymeric materials in sheet form that are capable of providing a rigid base for the release liner are suitable for use in the present invention. For example, a preferred polymeric material is a polyethylene terephthalate at a thickness range of about 50 microns to about 125 microns.

The use of a support layer in the release liner of the present invention may require the inclusion of a tie layer positioned between the metal layer and the support layer. The tie layer functions as a bonding agent to anchor the metal layer to the support layer. The composition of the tie layer is generally a polymeric material, such as an epoxy or polyamide applied onto the support layer, the metal layer, or both as a thin film or laminated such that the support layer and the metal layer are bonded together. Preferably, the tie layer is a thermoplastic or thermoset adhesive applied, for example, as a hot melt adhesive, a laminating adhesive, or a pressure-sensitive adhesive. The tie layer could include extruded hot melt adhesives with adequate thermal stability to withstand subsequent processing conditions. Generally, the tie layer must be thermally stable at temperatures at which the release liner and attached article are processed. The processing temperature is generally in he range of up to about 175° C. and typically between about 80° C. to about 150° C. Other bonding polymers generally recognized by those skilled in the art can be suitable for use with the present invention. Preferably, the tie layer included in the release liner has a thickness up to 15 microns.

Figure 2:
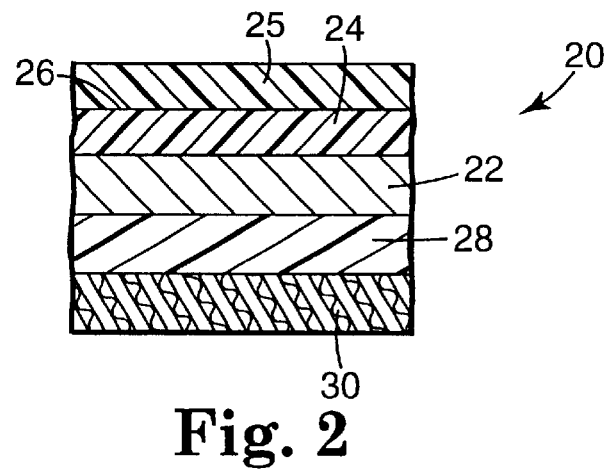
FIG. 2 is a segmented, cross-sectional view of another embodiment of the release liner of the present invention.

FIG. 2 illustrates the release liner 20 of the present invention in which a tie layer 28 and support layer 30 are utilized. The release liner 20 includes a metal layer 22 having a release agent 24 attached to the metal layer 22. The release agent 24 has a surface 26 for receiving an article 25. The tie layer 28 functions as a bonding agent to attach the metal layer 22 to the support layer 30.

An optional embodiment of the present invention includes the use of an intermediate layer positioned between the metal layer and the release agent. An intermediate layer may be utilized to permit a better deposition of a release agent onto the liner. The intermediate layer is generally a polymeric material that may be coated over the metal layer. An example of an intermediate layer would include a layer of polyethylene. When utilizing an intermediate layer, the bond between the intermediate layer and the release agent must be stronger than the bond between the article and the release agent in order to prevent the separation of the intermediate layer from the release liner when the article, or a cut portion thereof, is pulled away from the release liner.

Another alternative embodiment of the present invention is the use of a water impermeable membrane attached to a paper support layer. Paper is a desirable material for the support layer because it is an economically efficient means for providing a proper rigid base for the release liner. However, paper has a tendency to lose moisture and curl under certain processing conditions. Therefore, it is desirable to coat the exposed surface of the paper support layer with a water impermeable membrane. Suitable materials for this purpose include polymeric materials such as polyethylene. The use of water impermeable materials prevents the rapid loss of moisture by the paper and helps to ensure that the paper will lay flat both during and after processing.

The release liner of the present invention can be supplied as a web of rolled material. A web enables the application or formation of the article onto a continuous roll. The article and the release liner can then be rolled back into a web for further processing or for final application. With adhesive backed articles, it is often desirable to first apply the adhesive onto the release liner before the application of the article onto the adhesive. Thus, in a web format, it is often necessary to apply a second layer of a release agent onto the release liner. The second release agent is applied onto a side of the liner opposite the first release agent. This permits both the winding of the material into a web and the subsequent unwinding without the adhesive adhering to the backside of the release liner. The second release agent should have a release value less than the release value of the first release agent. Preferably, the ratio of the release value of the first release agent to the release value of the second release agent is about 2:1 to about 3:1. Thus, the release liner of the present invention may temporarily include an exposed adhesive on an outer surface of the release liner during the article formation process. However, an outer exposed adhesive layer temporarily applied onto the release liner is not considered part of the release liner because it is subsequently removed from the liner upon final application of the article.

Figure 3:
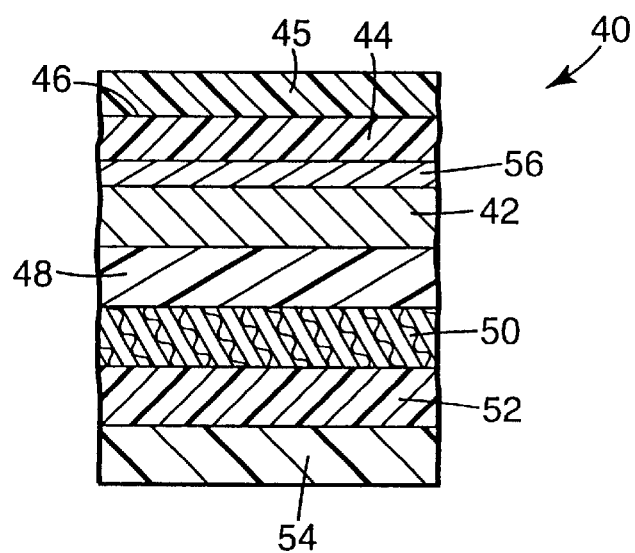
FIG. 3 is a segmented, cross-sectional view of another embodiment of the release liner of the present invention.

FIG. 3 depicts another embodiment of the present invention. The release liner 40 has a metal layer 42 and a first release agent 44. An intermediate layer 56 is positioned between the metal layer 42 and the release agent 44. The release agent 44 has a surface 46 that is suitable for releasably receiving an article 45. A tie layer 48 is utilized to bond the metal layer to a paper support layer 50. A water impermeable layer 52 of a high density polyethylene is applied onto the paper support layer 50. A second release agent 54 is applied to the release liner 40 over the water impermeable layer 52 on an opposing side of the release liner 40 from the first release agent 44.

The article applied to the release liner of the present invention may be provided in various forms or formats. For purposes of this invention, an article is defined as one or more layers or objects that can be laser cut and releasably received by the release agent of the present invention. The articles may include various materials that are suitable for cutting with a laser. The article is preferably selected from the group consisting of adhesive backed articles and non-adhesive backed articles, such as, for example, vinyl articles or urethane articles.

Additionally, the articles used in conjunction with the present invention can include indicia applied onto a base layer to form a decorative article. Indicia includes any distinctive marks or representations. In the present invention, indicia could include such items as printed graphics or three-dimensional graphics. Printed indicia may be applied onto the article, for example, with solvent based inks, water-based inks, UV inks, or powder inks. The printed indicia may be applied through various processes including screen printing, flexo-graphic printing, gravure printing, digital printing, off-set printing, and pad printing.

Three dimensional graphics can also be applied onto the article or may, by themselves, serve as the article. Three dimensional graphics can include for example, a cured polyurethane body with a tie layer bonded to the polyurethane. An adhesive is then applied to the opposing surface of the tie layer. Example of three-dimensional graphics include those disclosed in EP 0392847, herein incorporated by reference. Other types and styles of indicia may also be utilized with the present invention. Alternatively, the article may include several different types or styles of indicia applied, or layered upon the article.

The method of the present invention involves the laser cutting of an article releasably adhered to the release liner of the present invention. The release liner, with the attached article, is positioned near a laser, for example on a cutting table with the laser positioned above the article and the release liner. The laser, once activated, is directed onto the article in a specified pattern or cutting line. The laser cuts through the article to the metal layer of the release liner. The metal layer is of sufficient thickness to prevent penetration through the metal layer. The laser would also cut through any intermediate layers between the article and the metal layer, if they are present in the release liner. For purposes of the invention, the laser may also cut through a portion of the metal layer without cutting completely through the metal layer. The partial cutting of the metal layer still accomplishes the objectives of the present invention as long as the metal layer does not fracture or break when a portion of the article is later removed from the release liner.

In accordance with the present invention, the properties of the laser and the metal layer are selected to achieve the objectives of the present invention. The type of laser, the laser strength, and the laser cutting speed are generally selected to permit the cutting of the article yet yield to the metal layer of the release liner. Those skilled in the art are capable of selectively matching a metal layer, at a certain thickness, to a specified laser so that the energy of the laser is dissipated, or reflected, without penetrating through the metal layer. Preferably, $CO_2$ lasers are utilized in cutting the articles contemplated by the present invention. However, other lasers may also be utilized. A preferred example of a metal layer and laser combination includes an aluminum metal layer of about 2 to about 7 microns applied onto a paper support layer and matched to a 500–1000 watt $CO_2$ laser with a cutting speed of about 75 centimeters per second.

In practicing the method of the present invention, a portion of the article is generally cut into a pattern or shape. The desired portion of the article is then later separated from the release liner for final application onto another object. With certain types of articles, such as raised lettering, it may be useful to utilize a premask layer applied over the articles to maintain the appropriate spacing for final application. The inventive release liner permits the removal of a cut portion of the article without any tearing of the release liner. Additionally, end use applications for the article may require the removal of an undesired cut portion of the article, thus leaving the desired portion directly on the release liner. The practice of removing the unwanted portion, often referred to as weeding, is advantageously accomplished without tearing the release liner.

The release liner and article may be supplied in either web or sheet form. The method of laser cutting the article is well suited for either form. Additionally with either form, it may be necessary after the cutting and weeding stages, to through-cut the article and release liner into smaller size sections for end use applications.

The following non-limiting examples further illustrate the present invention. The particular materials and amounts recited in these examples, as well as other conditions and details, are to be interpreted broadly in the art and should not be construed to unduly restrict or limit the invention in any way.

EXAMPLE 1

An aluminum metal layer was laminated to Polyslik™ release liners from Rexam of Charlotte, N.C. The metal layer was approximately 2 microns thick. The lamination of the metal layer was accomplished by first applying silicone tape, 8403HD8112-7 tape sold by Minnesota Mining and Manufacturing Company of St. Paul, Minn., onto the release liner. A spray adhesive, marketed as Super 77 from Minnesota Mining and Manufacturing Company of St. Paul, Minn., was applied over the silicone tape. The metal layer was then applied onto the adhesive. A coating of a release agent was then sprayed onto the release liner over the metal layer. The release agent was Wet Proof Heavy Duty Outdoor Water Protection marketed under Kiwi Brands by the Sara Lee Corporation of Douglasville, Pa. An adhesive backed article was transferred and laminated onto the release liner. The adhesive backed article was prepared as disclosed in Example 1 of EP 0392847, previously incorporated by reference. The article was prepared by vacuum forming a 100 micron thick vinyl film to produce a three dimensional molded film in the shape of a series of letters. The hollow back portion of the molded film was then filled with a 2-part urethane composition. The series of letters extended about 4000 microns above the base surface. A 375 micron thick pressure-sensitive adhesive foam attached to a thin thermoplastic polyamide film was placed over the polyurethane composition in the mold with the polyamide film in contact with the urethane composition. The urethane composition was then allowed to cure in the mold at about 55° C. for about 3 minutes. The article having a pressure-sensitive adhesive was then removed from the mold and the adhesive side of the article was laminated to the release coated side of the release liner.

The release liner carrying the adhesive backed article was placed on a cutting table under a laser cutting system with a dynamic beam. The liner and article were placed about 45 centimeters from the laser. The system utilized a $CO_2$ laser at a strength of about 500 watts and a cutting speed of about 75 centimeters per second. The laser was utilized to cut the 100 micron thick vinyl film around the perimeter of the dimensional lettering. The laser cut through the article but did not penetrate into the metal foil of the release liner.

EXAMPLE 2

In the present Example, a release liner was formed utilizing a layered matrix of a first silicone release agent, a high density polyethylene layer at a thickness of 10 about 25 microns, an aluminum foil layer at a thickness of about 5 microns, a combined low density polyethylene/ethylene acrylic acid layer at a thickness of about 25 microns, a paper layer at a thickness of about 125 microns, and a second silicone release agent. The first silicon release agent had a release value of about 45 grams/cm and the second silicone release agent had a release value of about 20 grams/cm. The release liner was formed as a web, but was cut into 30 cm by 32.5 cm sheets for purposes of this Example. An article was applied onto the surface of the release liner over the coating of the first release agent. The article was an adhesive backed article comparable in construction and thickness to that disclosed in Example 1. The pressure sensitive adhesive of the article was releasably attached to the release liner.

The release liner and attached decorative article were placed on a cutting surface at about 45 centimeters below a $CO_2$ laser. The laser was operated at a 500 watts and a cutting speed of about 76 centimeters per second. The laser was used to kiss-cut around the perimeter of the indicia. The laser provided a precise cut without cutting through the metal foil layer. Individual letters were subsequently removed from the liner without any tearing or pulling away of the liner.

From the above disclosure of the general principles of the present invention and the preceding detailed description, those skilled in this art will readily comprehend the various modifications to which the present invention is susceptible. therefore, the scope of the invention should be limited only by the following claims and equivalents thereof.

What is claimed is:

1. A decorative article assembly, comprising,
   (a) a release liner containing a metal layer and a release agent attached to a side of said metal layer;
   (b) an article releasably attached to said release agent wherein said metal layer has a thickness sufficient to prevent a laser from penetrating through said metal layer as the laser cuts through said article, and said article includes a laser cut portion forming a perimeter a decorative article.

2. The decorative article assembly as recited in claim 1, wherein said decorative article can be separated from said release liner without a portion of said metal layer separating with said laser cut portion.

3. The decorative article assembly as recited in claim 1, further comprising an intermediate layer bonded between said metal layer and said release agent, wherein said decorative article can be separated from said release liner without a portion of said metal layer or said intermediate layer separating with said laser cut portion.

4. The decorative article assembly as recited in claim 1, wherein said decorative article includes indicia on a side opposite the side attached to the release agent.

5. The decorative article assembly as recited in claim 4, wherein the indicia are three dimensional.

6. The decorative article assembly as recited in claim 1, wherein said article includes a plurality of layers.

7. The decorative article assembly as recited in claim 1, wherein said article has an adhesive on one side and said adhesive is releasably adhered to said release agent.

8. The decorative article assembly as recited in claim 7, wherein said adhesive is a pressure-sensitive adhesive.

9. A method for laser cutting an article releasably adhered to a release liner, comprising:
   laser cutting an article releasably adhered to the release liner of claim 1 into a laser cut portion forming a decorative article.

10. The method as recited in claim 9, wherein the release liner further comprises an intermediate layer positioned between the metal layer and the release agent, and said method includes separating the laser cut portion of the article from the release liner without a portion of the metal layer or the intermediate layer separating with the laser cut portion.

11. The method as recited in claim 9, further comprising:
   separating the laser cut portion of the article from the release liner without a portion of the metal layer separating with the laser cut portion.

* * * * *

UNITED STATES PATENT AND TRADEMARK OFFICE
CERTIFICATE OF CORRECTION

PATENT NO.   : 6,355,322 B1
DATED        : March 12, 2002
INVENTOR(S)  : Golledge, Adrian D.

It is certified that error appears in the above-identified patent and that said Letters Patent is hereby corrected as shown below:

<u>Column 4,</u>
Line 47, the term "in he range" should read -- in the range --.

<u>Column 8,</u>
Line 27, after the word "perimeter" please insert -- of --.

Signed and Sealed this

Eleventh Day of February, 2003

JAMES E. ROGAN
*Director of the United States Patent and Trademark Office*